US009097678B2

(12) United States Patent
Schwab et al.

(10) Patent No.: US 9,097,678 B2
(45) Date of Patent: Aug. 4, 2015

(54) METHOD FOR REMOVING SULFUR-COMPRISING COMPOUNDS FROM A HYDROCARBONACEOUS GAS MIXTURE

(71) Applicant: BASF SE, Ludwigshafen (DE)

(72) Inventors: Ekkehard Schwab, Neustadt (DE); Heiko Urtel, Bobenheim-Roxheim (DE); Schaefer Alexander, Limburgerhof (DE)

(73) Assignee: BASF SE (DE)

( * ) Notice: Subject to any disclaimer, the term of this patent is extended or adjusted under 35 U.S.C. 154(b) by 0 days.

(21) Appl. No.: 13/667,567

(22) Filed: Nov. 2, 2012

(65) Prior Publication Data

US 2013/0115707 A1 May 9, 2013

Related U.S. Application Data

(60) Provisional application No. 61/554,991, filed on Nov. 3, 2011.

(51) Int. Cl.
| | |
|---|---|
| *G01N 21/78* | (2006.01) |
| *G01N 21/75* | (2006.01) |
| *G01N 21/00* | (2006.01) |
| *B01J 20/08* | (2006.01) |
| *B01J 20/18* | (2006.01) |
| *B01D 53/02* | (2006.01) |
| *B01J 20/30* | (2006.01) |
| *B01J 20/32* | (2006.01) |
| *C10L 3/10* | (2006.01) |
| *B01J 20/02* | (2006.01) |
| *B01J 20/28* | (2006.01) |
| *B01D 53/04* | (2006.01) |
| *H01M 8/06* | (2006.01) |
| *C10L 3/12* | (2006.01) |

(52) U.S. Cl.
CPC ............... *G01N 21/78* (2013.01); *B01D 53/02* (2013.01); *B01D 53/04* (2013.01); *B01D 53/0454* (2013.01); *B01J 20/0214* (2013.01); *B01J 20/0218* (2013.01); *B01J 20/0222* (2013.01); *B01J 20/0244* (2013.01); *B01J 20/08* (2013.01); *B01J 20/18* (2013.01); *B01J 20/28042* (2013.01); *B01J 20/3078* (2013.01); *B01J 20/3204* (2013.01); *B01J 20/3236* (2013.01); *B01J 20/3291* (2013.01); *C10L 3/103* (2013.01); *C10L 3/12* (2013.01); *H01M 8/0675* (2013.01); *B01D 2253/102* (2013.01); *B01D 2253/108* (2013.01); *B01D 2256/24* (2013.01); *B01D 2257/304* (2013.01); *B01D 2257/306* (2013.01); *B01D 2257/308* (2013.01); *B01D 2259/40084* (2013.01); *Y02E 60/50* (2013.01); *Y10T 436/18* (2015.01)

(58) Field of Classification Search
CPC ....... G01N 21/78; G01N 21/77; G01N 21/75; G01N 21/00; Y10T 436/00; Y10T 436/18; Y10T 436/21; Y10T 436/218
USPC .......................................................... 436/119
See application file for complete search history.

(56) References Cited

U.S. PATENT DOCUMENTS

| | | | |
|---|---|---|---|
| 2001/0000143 A1 | 4/2001 | Bausch et al. | |
| 2001/0014304 A1 | 8/2001 | Satokawa et al. | |
| 2002/0028505 A1* | 3/2002 | Sakai et al. | ................ 435/299.1 |
| 2004/0224836 A1 | 11/2004 | Vempati et al. | |
| 2005/0161342 A1 | 7/2005 | Carson et al. | |
| 2011/0200507 A1 | 8/2011 | Steiner et al. | |

FOREIGN PATENT DOCUMENTS

| | | | | |
|---|---|---|---|---|
| CN | 101299465 A | 11/2008 | | |
| CN | 101484802 A | 7/2009 | | |
| CN | 102170953 A | 8/2011 | | |
| EP | 1 121 977 A2 * | 8/2001 | ............... | B01J 20/18 |
| EP | 1988593 A1 | 11/2008 | | |
| WO | WO-2008007899 A1 | 1/2008 | | |
| WO | WO-2010023249 A1 | 3/2010 | | |
| WO | WO-2011033280 A1 | 3/2011 | | |
| WO | WO-2011031883 A3 | 7/2011 | | |

OTHER PUBLICATIONS

Westmoreland P. et al, Evaluation of Candidate Solids for High-Temperature Desulfurization of Low-Btu Gases, Environmental Science & Technology, 1976, vol. 10, No. 7, pp. 659-661.*
Jung, et al. "Adsorptive removal of tert-butylmercaptan and tetrahydrothiophene using microporous molecular sieve ETS-10" Applied Catalysis B: Environmental 100 (2010) pp. 264-270.
Lee, et al., "Adsorptive removal of tetrahydrothiophene (THT) and tert-butylmercaptan (TBM) using Na—Y and AgNa—Y zeolites for fuel cell applications" Applied Catalysis A: General 334 (2008) pp. 129-136.
Park, et al. "Interactions Between Tetrahydrothiophene (THT) and Silver Species in AgNa—Y" Journal of Nanoscience and Nanotechnology, vol. 10, (2010) pp. 203-210.
Song, et al. "Hydrogen and Syngas Production and Purification Technologies" Chapter 5, Wiley 2010, pp. 219-310.
International Search Report for PCT/IB2012/056011, mailing date Mar. 14, 2013.

* cited by examiner

*Primary Examiner* — Christine T Mui
(74) *Attorney, Agent, or Firm* — Drinker Biddle & Reath LLP

(57) ABSTRACT

A method for removing sulfur-comprising compounds from a hydrocarbonaceous gas mixture, in which an adsorber material is brought into contact with the hydrocarbonaceous gas mixture, wherein the adsorber material comprises a material that adsorbs sulfur-comprising compounds and, in addition, comprises at least one transition metal compound which changes color thereof by reaction with the sulfur-comprising compounds.

14 Claims, No Drawings

METHOD FOR REMOVING SULFUR-COMPRISING COMPOUNDS FROM A HYDROCARBONACEOUS GAS MIXTURE

CROSS-REFERENCE TO RELATED APPLICATIONS

This application claims the benefit of U.S. Provisional Application 61/554,991, filed Nov. 3, 2011, which is incorporated herein by reference.

The invention relates to a method for removing sulfur-comprising compounds from a hydrocarbonaceous gas mixture using an adsorber material, in which the degree of loading of the adsorber material can be determined by optical examination.

In fuel cells, the energy which is liberated on the reaction of a fuel with oxygen can be converted directly into electrical energy. By way of this direct conversion of chemical energy to electrical energy, fuel cells offer the possibility of achieving higher degrees of efficiency than conventional combined heat and power machines. In modern fuel cell systems, natural gas, but also liquid gas (LPG), is frequently used. These gases are converted in a reformer by reformation into hydrogen-rich and carbon monoxide-rich synthesis gas which serves as fuel for the fuel cell.

Natural gas has, especially in highly industrialized countries, the advantage of extensive availability, since a dense supply grid exists. In addition, natural gas has a high hydrogen:carbon ratio which is favorable for hydrogen production. The expression "natural gas" here represents a multiplicity of possible gas compositions which can differ greatly depending on the gas field. Natural gas can comprise virtually exclusively methane ($CH_4$), but can also comprise considerable amounts of higher hydrocarbons. The expression "higher hydrocarbons" in this case is taken to mean all hydrocarbons from ethane ($C_2H_6$), regardless of whether they are linear saturated and unsaturated, cyclic or aromatic hydrocarbons. Typically, the fractions of higher hydrocarbons in the natural gas decrease with higher molecular weight and higher vapor pressure.

In addition to the higher hydrocarbons, further gas minor components and impurities occur in the natural gas. In this context, mention may be made, in particular, of sulfur compounds of natural origin which can occur at low concentrations. Examples thereof are hydrogen sulfide ($H_2S$), carbonyl sulfide (COS), carbon disulfide ($CS_2$) and light organosulfur compounds such as, for example, MeSH.

In addition to the naturally occurring sulfur compounds, further sulfur compounds, termed odorants, are added to the natural gas for safety reasons. Natural gas is usually odorless and nontoxic, but in combination with air can lead to explosive mixtures. In order to be able to notice an uncontrolled escape of natural gas immediately, natural gas is admixed with intensely odorous substances at a low concentration which cause the characteristic odor of natural gas. Since there is a risk of becoming accustomed to the odor of the odorant on escape of the gas from a small gas leak, the addition of the odorant is greatly increased for short times at regular intervals.

The odorization of natural gas is prescribed by law in most countries—together with the odorants which are to be used. In some countries, such as, for example, the United States of America, frequently mercaptans (R—S—H, R=alkyl radical), such as tert-butylmercaptan (TBM) or ethylmercaptan, are used as odorants, whereas in the member states of the European Union, usually cyclic sulfides such as tetrahydrothiophene (THT) are used. On account of chemical reactions that possibly proceed, sulfides, such as dimethyl sulfide, and/or disulfides can be formed from mercaptans, which sulfides must likewise be removed.

Together with the naturally occurring sulfur compounds, there are therefore a multiplicity of various sulfur compounds in the natural gas. The differing regulations for the composition of natural gas usually permit up to 100 ppm of sulfur compounds in the natural gas. The situation is similar for LPG as feedstock. LPG, which comprises as main components propane and butane, must, just like natural gas, be admixed with sulfur-comprising compounds as odor markers.

The sulfur-comprising compounds in natural gas or LPG can lead to severe and irreversible poisoning of the catalysts in a fuel cell or reformer. For this reason, the hydrocarbonaceous gases which are fed to the fuel cell must be purified from all sulfur-comprising compounds. Fuel cell systems, for this reason, always comprise a desulfurization unit for the natural gas or LPG used.

On an industrial scale, natural gas is predominantly desulfurized by catalytic hydrogenation with addition of hydrogen. This desulfurization method, however, is not expedient to be employed in small and very small scale applications, especially fuel cells in the domestic sector, and so here recourse is principally had to adsorptive methods for purifying the hydrocarbonaceous gas stream.

Adsorptive methods are distinguished by a simple process procedure. The hydrocarbonaceous gas stream in this case is simply passed over an adsorber which is usually present in the form of a fixed bed. The sulfur-comprising compounds are retained on this adsorber owing to their physicochemical properties. During the operating period, continuous loading of the adsorber proceeds so that ultimately after exhaustion of the uptake capacity, no sulfur-comprising compounds can be adsorbed any longer. On exhaustion of the uptake capacity, breakthrough of the sulfur-comprising compounds then occurs.

The expression adsorber material is defined in the present invention as a material that can bind sulfur-comprising compounds reversibly or irreversibly or can react them to form other compounds.

With the purpose of producing adsorber materials of a higher uptake capacity for sulfur-comprising compounds, many materials have been investigated. Those which have proved to be suitable are:
  activated carbon, optionally with promoters
  metal oxides, mixed metal oxides
  zeolites, optionally modified with metals or promoters
A survey of the desulfurization adsorbers suitable for natural gas is given by Chunshan Song and Xiaoliang Ma in "Hydrogen and Syngas Production and Purification Technologies" Chapter 5, pp. 219-311, Wiley 2010.

WO 2011/033280 A1 discloses the use of ZnO for desulfurization.

WO 2011/031883 A2 and Hwahak Konghak (2010), 48, 4, 534-539 disclose the use of zeolites for desulfurization.

Hwan et al. (APPLIED CATALYSIS B-ENVIRONMENTAL, 100, 1-2, pp. 246-270), Lee et al. (JOURNAL OF NANOSCIENCE AND NANOTECHNOLOGY, 10, 1, pp. 203-210) and Chul et al. (APPLIED CATALYSIS A-GENERAL, 334, 1-2, pp. 129-139) describe the use of zeolites and doped zeolites for desulfurization.

In addition to a high uptake capacity of the adsorber materials for sulfur-comprising compounds, for a broad application, it is also of importance to exhaust this uptake capacity as completely as possible without risking a sulfur breakthrough. This is because such a breakthrough can lead to irreversible deactivation of the catalysts in the reformer and in the fuel cell and thereby damage the application. In industrial scale applications, the sulfur breakthrough is often prevented by the hydrocarbonaceous gas mixture exiting from the adsorber being studied by analytical methods such as gas chromatography, infrared spectroscopy, XRD analysis, or the like, in defined time intervals for the sulfur content thereof. If the sulfur content exceeds a specified threshold value, the adsorber material is exchanged or regenerated.

The adsorptive methods described in the prior art for desulfurizing hydrocarbonaceous gas mixtures are disadvantageous in that the degree of loading of the adsorber material of sulfur-comprising compounds cannot be determined simply and directly and a high exhaustion of the uptake capacity, without risking sulfur breakthrough, is only possible by way of special analytical resources. There is therefore a need for adsorptive methods which make possible simple and direct determination of the degree of loading of the adsorber material of sulfur-comprising compounds, for example by optical examination.

The object of the present invention is therefore to provide a method for the desulfurization of hydrocarbonaceous gas mixtures by adsorption, in which the degree of loading of the adsorber material of sulfur-comprising compounds can be determined by optical examination of the adsorber material. The adsorber material in this process must at the same time ensure the removal of sulfur-comprising compounds from a hydrocarbonaceous gas mixture and indicate the degree of loading by a color change. The object in particular of the present invention is to provide such a method for desulfurization by adsorption of hydrocarbonaceous gas mixtures, in which all of the usual sulfur-comprising compounds are removed from the hydrocarbonaceous gas mixture and any of the sulfur-comprising compounds causes a color change of the adsorber material.

The object is achieved by a method for removing sulfur-comprising compounds from a hydrocarbonaceous gas mixture, in which an adsorber material is brought into contact with the hydrocarbonaceous gas, wherein the adsorber material comprises a material A that adsorbs sulfur-comprising compounds and, in addition, comprises at least one transition metal compound B which changes color thereof by reaction with the sulfur-comprising compounds.

In the method according to the invention, the degree of loading of the adsorber material of sulfur-comprising compounds may be determined simply and directly without special analytical resources, by optical examination. The adsorber material ensures the removal of sulfur-comprising compounds from the hydrocarbonaceous gas mixture and indicates the degree of loading by a color change. Using the method according to the invention, all the usual sulfur-comprising compounds can be removed from the hydrocarbonaceous gas mixture. Each of these usual sulfur-comprising compounds in this case can cause a color change of the adsorber material.

The adsorber material according to the invention generally comprises 0.01 to 40% by weight, preferably 0.01 to 30% by weight, and particularly preferably 0.01 to 20% by weight, of at least one transition metal compound B which changes color thereof by reaction with the sulfur-comprising compounds, and 60 to 99.99% by weight, preferably 70 to 99.99% by weight, and particularly preferably 80 to 99.99% by weight, of a material A adsorbing sulfur-comprising compounds.

Suitable transition metal compounds are compounds of outer and inner transition metals which change color thereof by reaction with the sulfur-comprising compounds. Suitable transition metal compounds are those containing a transition metal of groups 5 to 7 of the Periodic Table of the Elements (Vi, Nb, Ta, Cr, Mo, Wi, Mn, Ic, Re). Preferably, the transition metal is selected from the group consisting of vanadium, chromium, manganese and molybdenum. Particularly preferably, the transition metal is selected from the group consisting of manganese and molybdenum. Suitable transition metal compounds are, in addition, inner transition metal compounds of inner transition metals (Lanthanides).

Suitable transition metal compounds here are those in which the transition metal is used in an oxidation state which is high for this transition metal. Preferably, the transition metal is used in an oxidation state $\geq 5$. For example, suitable transition metal compounds are those of the following transition metals in the oxidation states stated in parentheses: vanadium(V), chromium(VI), molybdenum(VI) and manganese(VII). Preferably, the transition metal is used in an oxidation state $\geq 6$. Suitable transition metals of these oxidation states are chromium(VI), molybdenum(VI), manganese(VII). Particular preference is given to molybdenum(VI) and manganese(VII).

Suitable transition metal compounds B of this type are transition metal oxides, oxoacids of the transition metal or salts of an oxoacid of the transition metal. Preferably, the transition metal compound is a transition metal oxide, or a salt of an oxoacid of the transition metal. In a preferred embodiment, the transition metal compound is a transition metal oxide. Particularly preferably, the transition metal oxide is $MoO_3$. In a further preferred embodiment, the transition metal compound is the salt of an oxoacid of the transition metal, particularly preferred is $KMnO_4$.

The transition metal compound B can optionally also adsorb sulfur-comprising compounds.

Suitable materials adsorbing sulfur-comprising compounds A are, for example, zinc oxide, mixtures which comprise, inter alia, zinc, nickel or copper, zeolites or activated carbons. Preferred materials adsorbing sulfur-comprising compounds are zinc oxide, mixtures which comprise, inter alia, zinc, nickel or copper, or zeolites. In a particularly preferred embodiment, the material adsorbing sulfur-comprising compounds is ZnO. In a further particularly preferred embodiment, the material adsorbing sulfur-comprising compounds is a zeolite. In a further particularly preferred embodiment, the material adsorbing sulfur-comprising compounds is a silver-doped zeolite. In a further particularly preferred embodiment, the material adsorbing sulfur-comprising compounds is silver-doped X-zeolite.

The adsorber material according to the invention can be produced as described hereinafter.

First, optionally, the material A adsorbing sulfur-comprising compounds is produced by generally known methods, for example by precipitation, soaking, mixing, kneading, sintering, spraying, spray drying, ion exchange or electroless deposition. The material adsorbing sulfur-comprising compounds can either be processed further directly in the form of powder, or first converted to shaped bodies, for example rods, extrudates or tablets.

The adsorber material according to the invention can be produced in many ways by generally known methods from the material adsorbing sulfur-comprising compounds and from the transition metal compound B. For example, simple mixing, extrusion, pan-grinding, tableting, soaking, optionally with subsequent calcinations, impregnation, optionally with subsequent calcinations, are suitable methods. Preferably, the adsorber material according to the invention is produced by soaking, optionally with subsequent calcinations, or by impregnation, optionally with subsequent calcinations.

In a preferred embodiment, the adsorber material according to the invention is produced by soaking rods of the material adsorbing sulfur-comprising compounds with the transition metal compound B.

In a further preferred embodiment, the adsorber material according to the invention is produced by impregnating rods of the material A adsorbing sulfur-comprising compounds with the transition metal compound B and subsequent calcination.

The adsorber material according to the invention is used in the form of powder or shaped bodies, such as rods, tablets, granules or extrudates. Preferably, the adsorber material according to the invention is used in the form of rods, tablets, granules or extrudates. Particularly preferably, the adsorber material according to the invention is used in the form of rods, tablets or extrudates.

The adsorber material according to the invention is used for removing sulfur-comprising compounds from a hydrocarbonaceous gas mixture. Preferably, the adsorber material according to the invention is used for removing sulfur-comprising compounds from a hydrocarbonaceous gas mixture with which at least one fuel cell is operated.

The method according to the invention is suitable for removing sulfur-comprising compounds from hydrocarbonaceous gas mixtures. Preferably, the hydrocarbonaceous gas mixture is natural gas or LPG. Particularly preferably, the hydrocarbonaceous gas mixture is natural gas.

The composition of natural gas can vary considerably depending on site of discovery. The main component of natural gas, however, is always methane, usually the fraction is at least 90% by volume. In addition, natural gas generally further comprises higher hydrocarbons such as ethane, propane, butane, pentane and ethene. LPG contains propane and butane as main components, and usually the fraction thereof is greater than 90% by volume. In addition, propene and butene are present in lower amounts.

Generally, the hydrocarbonaceous gas mixture comprises in total 1 to 500 ppm, preferably 5 to 250 ppm, of sulfur-comprising compounds. Frequently, sulfur-comprising compounds are present in the following amounts:

| | |
|---|---|
| $H_2S$ | 0.5 to 50 ppm; |
| Mercaptans | 0 to 100 ppm, preferably 1 to 100 ppm; |
| Sulfides | 0 to 100 ppm, preferably 1 to 100 ppm; |
| Tetrahydrothiophene | 0 to 20 ppm, preferably 0.5 to 20 ppm. |

Usually in the hydrocarbonaceous gas mixtures that are to be purified, mercaptans that are to be encountered are ethylmercaptan and tert-butylmercaptan, a usual sulfide is dimethyl sulfide.

In the method according to the invention, the hydrocarbonaceous gas mixture contaminated by sulfur-comprising compounds can be passed over the adsorber material according to the invention at a temperature of −50 to 150° C., preferably −20 to 80° C., particularly preferably 0 to 80° C., in particular 15 to 60° C., and at a pressure of 0.1 to 10 bar, preferably 0.5 to 4.5 bar, particularly preferably 0.8 to 2.0 bar.

Advantageously, the hydrocarbonaceous gas mixture is passed in this case in straight flow through the adsorber material according to the invention. The method is operated particularly preferably at 50° C. and atmospheric pressure.

The uptake capacity of the adsorber material for a sulfur component is calculated from the mean concentration of the test gas of this sulfur component and the time after which the first sulfur-comprising compound is detected in online-GC. A generally valid formula is: capacity [g/l]=(concentration [mg/m³]×gas volume [m³/h]×running time [h])/(volume of catalyst [m³]×1 000 000). Running time is taken to mean the time up to which no sulfur compound is detected in the GC The gas volume corresponds to the test gas stream under standard conditions.

The sulfur-comprising compounds can be removed using the method according to the invention for removing sulfur-comprising compounds from a hydrocarbonaceous gas mixture to below the limit of detection of 0.04 ppm. Therefore, the method according to the invention is outstandingly suitable, in particular, for use in fuel cell systems.

In the method according to the invention, the adsorber material according to the invention changes color by reaction of the transition metal compound with the sulfur-comprising compounds and thereby enables determination of the degree of loading by optical examination. In particular, the reduction is effected by any of the sulfur-comprising compounds comprising hydrogen sulfide, tetrahydrothiophene, dimethyl sulfide, ethylmercaptan and tert-butylmercaptan.

In combination with a fuel cell system, the method according to the invention can be connected upstream of reforming. In this case the hydrocarbonaceous gas mixture that is purified from sulfur-comprising compounds can be fed directly into the reformer for obtaining hydrogen, or directly into the fuel cell. In this case the method according to the invention is suitable for all known types of fuel cells such as low-temperature and high-temperature PEM fuel cells, phosphoric acid fuel cells (PAFC), MCFC fuel cells (molten carbonate) and high-temperature fuel cells (SOFC).

The method according to the invention is suitable for use in stationary and mobile applications. Preferred applications in the stationary sector are, for example, fuel cell systems for simultaneous generation of power and heat, such as combined heat and power plants (CHP plant), preferably in the supply of domestic energy. In addition, the system is suitable for purifying gas streams for the desulfurization of natural gas for gas engines. For application in the non-stationary sector, the method can be used for purifying hydrocarbons for fuel cells in cars, trucks, buses or locomotives, preferably cars and trucks, particularly preferably cars. It is irrelevant in this case whether the fuel cells are used only for on-board power generation or for drive.

In the method according to the invention, the adsorber material according to the invention can be used alone or in combination with other adsorber materials suitable for removing sulfur-comprising compounds from hydrocarbonaceous gas mixtures.

In one embodiment of the invention, the adsorber material according to the invention is situated in an exchangeable desulfurization cartridge having a built-in viewing window. The built-in viewing window can in this case consist, for example, of glass, perspex or epoxy resin. The viewing window can have differing proportions and sizes and be arranged at various positions of the desulfurization cartridge. Suitable viewing windows are, for example, those which extend over the entire longitudinal direction of the cartridge, or viewing windows which make possible at least the view of part of the adsorber material according to the invention which shows a color change just before the sulfur breakthrough. The desulfurization cartridge can also comprise two or more viewing windows which are arranged one behind the other in the longitudinal direction of the cartridge. Furthermore, the desulfurization cartridge itself can comprise wholly or partly transparent material. The exchangeable desulfurization cartridge may be integrated simply and flexibly into the above-mentioned stationary and mobile applications. Suitable cartridges are, for example, cylindrical containers having screwin connections, into which gas-tight quick couplings may be screwed. The gas-tight quick couplings can also be mounted directly on the container. Details for the construction of such desulfurization cartridges are given in WO 2010/023249.

As soon as it is established in the optical examination that the uptake capacity of the adsorber material according to the invention in the desulfurization cartridge is virtually completely exhausted, the desulfurization cartridge can be exchanged without problem and rapidly, without needing to perform structural changes to the relevant application. The cartridge may therefore be simply replaced by a new cartridge comprising fresh adsorber material according to the invention.

Preferably, the ratio of length to diameter of the desulfurization cartridge at a given cartridge volume V which, in turn, results from the density of the adsorber material, the specific capacity of the adsorber material and the desired total capacity (=total amount of sulfur-comprising components to be bound) is selected such that the pressure drop ΔP to be set over the entire length L of the cartridge is less than the line pressure at which the hydrocarbonaceous gas mixture that is to be purified is pressurized. The maximum possible length L of the cartridge is therefore a function of the specific pressure drop of the adsorber material and the desired total adsorption capacity for a given adsorber material. From this length L and the required total volume V, there results the diameter D of the cartridge.

The preferred cartridge layout of the exchangeable desulfurization cartridge may also be described by the formula hereinafter:

$$i = \Delta P^* \cdot \frac{V}{L \cdot D \cdot c}$$

where
ΔP*=specific pressure drop [in kPa/m]
V=cartridge volume [l]
L=cartridge length [m]
D=equivalent diameter of the cartridge [m]
c=averaged fractional capacity.

The equivalent diameter D in this case is the diameter of the circular cross sectional area which corresponds to the cartridge cross sectional area. The averaged fractional capacity c is given by:

$$c = x_1 \cdot c_1 + x_2 \cdot c_2 + \ldots + x_n \cdot c_n$$

where $x_n = V_n/V$ and $c_n$=capacity of the adsorber n.

The ratio of L/D is preferably between 1.0 and 25. The value of the parameter i is preferably between 0 and 100.

Such a desulfurization cartridge is distinguished in that the minimum pressure drop on account of its dimensions permits an efficient utilization of the adsorber volume. This leads to best possible use of the adsorber material used for the greatest possible service life.

The invention will be described in more detail with reference to the examples hereinafter.

EXAMPLES

Example 1

A 5% strength by weight solution of $KMnO_4$ is made up. The ZnO rods (water uptake=1.63 ml/g) are placed in a spray disk and the $KMnO_4$ solution is sprayed onto the rotating ZnO rods up to 15% water uptake. After completion of the soaking, stirring is continued for a further 30 minutes. The resultant rods are dried for 12 hours at 85° C.

Example 2

A 2% strength by weight solution of $KMnO_4$ is made up. The X-zeolite rods (water uptake=0.67 ml/g) are placed in a spray disk and the $KMnO_4$ solution is sprayed onto the rotating X-zeolite rods up to 15% water uptake. After completion of the soaking, stirring is continued for a further 30 minutes. The resultant rods are dried at 85° C. for 12 hours.

Example 3

A 1% strength by weight solution of $KMnO_4$ is made up. The silver-doped X-zeolite rods (silver loading between 0.5 and 20% by weight) (water uptake=0.73 ml/g) are placed in a spray disk and the $KMnO_4$ solution is sprayed onto the rotating silver-doped X-zeolite rods up to 15% water uptake. After completion of the soaking, stirring is continued for a further 30 minutes. The resultant rods are dried for 12 hours at 85° C.

Example 4

A soaking solution is produced by completely dissolving 100 g of ammonium heptamolybdate in a mixture comprising 156 ml of deionized water and 34 ml of $NH_3$ water (25% strength) (final density of the solution between 1.15 and 1.35). This solution is then sprayed onto the ZnO rods (target content $MoO_3$ on rods: 10 to 20% by weight) with continuous recirculation. After completion of the soaking, stirring is continued for a further 30 minutes. The resultant soaked rods are calcined in a drying cabinet according to the following procedure: the furnace is preheated to 200° C. and the material kept at this temperature for 4 hours. Thereafter, the temperature is elevated to 520° C. (heating-up rate 10° C./min) and the temperature is maintained for 4 hours. For completion, the temperature is brought to 560° C. at a rate of 2° C./min. Finally, the material is cooled to room temperature and is ready for use.

Example 5

A soaking solution is produced by completely dissolving 100 g of ammonium heptamolybdate in a mixture comprising 156 ml of deionized water and 34 ml of $NH_3$ water (25% strength) (final density of the solution between 1.15 and 1.35). This solution is then sprayed onto the $Al_2O_3$ rods (target content $MoO_3$ on rods: 10 to 20% by weight) with continuous recirculation. After completion of the soaking, stirring is continued for a further 30 minutes. The resultant soaked rods are calcined in a drying cabinet according to the following procedure: the furnace is preheated to 200° C. and the material is maintained at this temperature for 4 hours. Thereafter the temperature is increased to 520° C. (heating-up rate 10° C./min) and the temperature is maintained for 4 hours. For completion, the temperature is brought to 560° C. at a rate of 2° C./min. Finally, the material is cooled to room temperature and is ready for use.

Example 6

A soaking solution is produced by completely dissolving 100 g of ammonium heptamolybdate in a mixture comprising 156 ml of deionized water and 34 ml of $NH_3$ water (25% strength) (final density of the solution between 1.15 and 1.35). This solution is then sprayed onto the X-zeolite rods (target content MoO₃ on rods: 10 to 20% by weight) with continuous recirculation. After completion of the soaking, stirring is continued for a further 30 minutes. The resultant soaked rods are calcined in a drying cabinet according to the following procedure: the furnace is preheated to 200° C. and the material maintained at this temperature for 4 hours. Thereafter the temperature is increased to 520° C. (heating-up rate 10° C./min) and the temperature is maintained for 4 hours. For completion, the temperature is brought to 560° C. at a rate of 2° C./min. Finally the material is cooled to room temperature and is ready for use.

Example 7

A soaking solution is produced by completely dissolving 100 g of ammonium heptamolybdate in a mixture comprising 156 ml of deionized water and 34 ml of NH₃ water (25% strength) (final density of the solution between 1.15 and 1.35). This solution is then sprayed onto the silver-doped X-zeolite rods (target content MoO₃ on rods: 10 to 20% by weight) with continuous recirculation. After completion of the soaking, stirring is continued for a further 30 minutes. The resultant soaked rods are calcined in a drying cabinet according to the following procedure: the furnace is preheated to 200° C. and the material maintained at this temperature for 4 hours. Thereafter the temperature is increased to 520° C. (heating-up rate 10° C./min) and the temperature is maintained for 4 hours. For completion, the temperature is brought to 560° C. at a rate of 2° C./min. Finally, the material is cooled to room temperature and is ready for use.

Use Tests

The adsorber materials are tested in a glass reactor (inner diameter: 1.5 cm). This permits color changes of the adsorber material to be observed during the experiment. As adsorber beds, volumes of 200 ml of material are charged. As gas supply, methane is available, the addition of which proceeds via a mass flow controller. Gas streams between 0 and 500 Nl/h are possible. Either by means of an optionally cooled substream saturator (for THT, ethylmercaptans, diethyl disulfide, tert-butyl sulfide and further liquid sulfur compounds) or via a test gas loop (for H₂S and COS), the corresponding sulfur-comprising compound is added to the natural gas. The gas comprising sulfurous compounds is passed through the adsorber bed. By way of a gas chromatograph, the composition of the gas is determined before and after the adsorber bed.

Course of the Tests

A compact bed of the adsorber material under test is charged into the glass reactor. The glass reactor is inserted into the test setup and charged by way of a gas stream that is enriched in advance with the sulfur-comprising compound under test. The control of the inlet and outlet compositions of the natural gas is determined by way of online-GC analysis.

| Material | Temp. [° C.] | GHSV [h⁻¹] | Concentration of the sulfur compound in the intake gas [vppm] | Capacity [g (sulfur compound)/ l (adsorber)] | Optical loading indication possible? |
|---|---|---|---|---|---|
| Example 1 | 50 | 6250 | 30 (H₂S) | 72 | yes |
| Example 1 | 50 | 3125 | 30 (H₂S) | 112 | yes |
| Example 2 | 50 | 6250 | 5 (THT) | 55 | yes |
| Example 2 | 50 | 6250 | 5 (DMS) | 32 | yes |
| Example 3 | 50 | 6250 | 5 (THT) | 72 | yes |
| Example 3 | 50 | 6250 | 5 (DMS) | 55 | yes |
| Example 4 | 50 | 6250 | 30 (H₂S) | 76 | yes |
| Example 4 | 75 | 6250 | 30 (H₂S) | 97 | yes |
| Example 4 | 100 | 6250 | 30 (H₂S) | 129 | yes |
| Example 4 | 150 | 6250 | 30 (H₂S) | 209 | yes |
| Example 4 | 50 | 6250 | 30 (EtSH) | 42 | yes |
| Example 4 | 50 | 6250 | 5 (THT) | 12 | yes |
| Example 4 | 50 | 6250 | 5 (DMS) | 8 | yes |
| Example 4 | 75 | 6250 | 30 (TBM) | 79 | yes |
| Example 5 | 50 | 6250 | 5 (THT) | 15 | yes |
| Example 6 | 50 | 6250 | 5 (THT) | 55 | yes |
| Example 7 | 50 | 6250 | 5 (THT) | 76 | yes |
| Al₂O₃ rods* | 50 | 6250 | 30 (H₂S) | 13 | no |
| ZnO rods* | 50 | 6250 | 30 (H₂S) | 63 | no |
| Zeolite rods* | 50 | 6250 | 5 (THT) | 53 | no |

*Comparative examples in each case without transition metal compound

RESULTS

All of the adsorber materials according to the invention described here are firstly suitable for removing sulfur-comprising compounds from a hydrocarbonaceous gas mixture and also indicate on the other hand, by color change, the loading of the adsorber material. In the case of the molybdenum-comprising adsorber materials: color change from colorless to brown, in the case of the KMnO₄-soaked adsorber materials: color change from violet to beige.

We claim:

1. A method for removing sulfur-comprising compounds from a hydrocarbonaceous gas mixture, in which an adsorber material is brought into contact with the hydrocarbonaceous gas mixture, wherein the adsorber material comprises a material A that adsorbs sulfur-comprising compounds and, in addition, comprises at least one transition metal compound B which changes color thereof by reaction with the sulfur-comprising compounds, wherein the transition metal of the transition metal compound B contains a metal selected from metals of groups 5 to 7 of the Periodic Table of the Elements, and wherein the transition metal is used in an oxidation state≥5; wherein the adsorber material comprises 10 to 40% by weight of the at least one transition metal compound B; wherein said hydrocarbonaceous gas mixture is contacted with said adsorber material at a temperature of −50 to 150° C. and a pressure of 0.1 to 10 bar.

2. The method according to claim 1, wherein the reaction is effected by any of the sulfur-comprising compounds comprising hydrogen sulfide, tetrahydrothiophene, dimethyl sulfide, ethylmercaptan and tert-butylmercaptan.

3. The method according to claim 1, wherein the transition metal is selected from the group consisting of vanadium, chromium, manganese and molybdenum.

4. The method according to claim 3, wherein the transition metal is selected from the group consisting of manganese and molybdenum.

5. The method according to claim 1, wherein the transition metal compound is a transition metal oxide.

6. The method according to claim 5, wherein the transition metal oxide is MoO₃.

7. The method according to claim 1, wherein the transition metal compound is a salt of an oxoacid of the transition metal.

8. The method according to claim 7, wherein the salt is KMnO4.

9. The method according to claim 1, wherein the material adsorbing sulfur-comprising compounds is zinc oxide.

10. The method according to claim 1, wherein the material adsorbing sulfur-comprising compounds is a zeolite.

11. The method according to claim 1, wherein the material adsorbing sulfur-comprising compounds is a silver-doped zeolite.

12. The method according to claim 1, wherein the hydrocarbonaceous gas mixture comprises 1 to 500 ppm of sulfur-comprising compounds.

13. The method according to claim 1, wherein the hydrocarbonaceous gas mixture is natural gas.

14. The method according to claim 13, wherein the hydrocarbonaceous gas mixture is subsequently fed to a fuel cell which is operated with the hydrocarbonaceous gas mixture.

* * * * *